(12) United States Patent
Hanson et al.

(10) Patent No.: US 11,026,422 B2
(45) Date of Patent: \*Jun. 8, 2021

(54) ACID/ANIONIC ANTIMICROBIAL AND VIRUCIDAL COMPOSITIONS AND USES THEREOF

(71) Applicant: Ecolab USA Inc., Saint Paul, MN (US)

(72) Inventors: Catherine Hanson, Saint Paul, MN (US); Junzhong Li, Saint Paul, MN (US); David D. McSherry, Saint Paul, MN (US); Stacy Fawbush, Saint Paul, MN (US); Kaitlin Lake, Saint Paul, MN (US); Gerard Hinrichs, Saint Paul, MN (US); Joshua Luedtke, Saint Paul, MN (US); Richard Staub, Saint Paul, MN (US); Derrick Anderson, Saint Paul, MN (US)

(73) Assignee: Ecolab USA Inc., Saint Paul, MN (US)

( \* ) Notice: Subject to any disclaimer, the term of this patent is extended or adjusted under 35 U.S.C. 154(b) by 0 days.

This patent is subject to a terminal disclaimer.

(21) Appl. No.: 16/142,798

(22) Filed: Sep. 26, 2018

(65) Prior Publication Data

US 2019/0090483 A1 Mar. 28, 2019

Related U.S. Application Data

(60) Provisional application No. 62/563,461, filed on Sep. 26, 2017.

(51) Int. Cl.
| | | |
|---|---|---|
| *A01N 37/36* | (2006.01) | |
| *A01N 25/30* | (2006.01) | |
| *A01N 31/02* | (2006.01) | |
| *A61L 2/18* | (2006.01) | |
| *A01N 31/08* | (2006.01) | |
| *A01N 47/28* | (2006.01) | |
| *A61L 2/22* | (2006.01) | |

(52) U.S. Cl.
CPC .............. *A01N 37/36* (2013.01); *A01N 25/30* (2013.01); *A01N 31/02* (2013.01); *A01N 31/08* (2013.01); *A01N 47/28* (2013.01); *A61L 2/18* (2013.01); *A61L 2/22* (2013.01); *A61L 2202/14* (2013.01); *A61L 2202/24* (2013.01)

(58) Field of Classification Search
CPC ........ A01N 37/36; A01N 25/30; A01N 31/08; A01N 47/28; A61N 31/02; A61L 2/18; A01L 2202/14; A01L 2202/24; A01L 2/22
See application file for complete search history.

(56) References Cited

U.S. PATENT DOCUMENTS

| | | | |
|---|---|---|---|
| 4,749,508 A | 6/1988 | Cockrell, Jr. et al. | |
| 4,897,304 A | 1/1990 | Hossain et al. | |
| 5,192,460 A | 3/1993 | Thomas et al. | |
| 5,234,719 A | 8/1993 | Richter et al. | |
| 5,330,769 A | 7/1994 | McKinzie et al. | |
| 5,336,426 A | 8/1994 | Rader et al. | |
| 5,364,551 A | 11/1994 | Lentsch et al. | |
| 5,436,008 A * | 7/1995 | Richter ................. | A01N 37/02 424/405 |
| 5,512,200 A * | 4/1996 | Garcia .................. | A61K 45/06 514/769 |
| 5,962,392 A | 10/1999 | Revell et al. | |
| 5,965,514 A | 10/1999 | Wierenga et al. | |
| 6,080,712 A | 6/2000 | Revell et al. | |
| 6,083,890 A | 7/2000 | Miskiel et al. | |
| 6,106,774 A | 8/2000 | Monticello et al. | |
| 6,121,224 A | 9/2000 | Fonsny et al. | |
| 6,150,557 A | 11/2000 | Adams et al. | |
| 6,197,738 B1 | 3/2001 | Regutti | |
| 6,197,814 B1 | 3/2001 | Arata | |
| 6,200,941 B1 | 3/2001 | Strandburg et al. | |
| 6,432,906 B1 | 8/2002 | Carlson et al. | |
| 6,472,358 B1 | 10/2002 | Richter et al. | |
| 6,495,506 B1 | 12/2002 | Massaux et al. | |
| 6,498,137 B1 | 12/2002 | Schalitz et al. | |
| 6,559,111 B2 | 5/2003 | Colurciello, Jr. et al. | |
| 6,583,103 B1 | 6/2003 | Klinkhammer | |
| 6,583,176 B2 | 6/2003 | Arata | |

(Continued)

FOREIGN PATENT DOCUMENTS

| | | |
|---|---|---|
| CA | 2562329 C | 12/2009 |
| CN | 101031634 A | 9/2007 |

(Continued)

OTHER PUBLICATIONS

Boomsma et al., "L-Lactic Acid—A Safe Antimicrobial for Home- and Personal Care Formulations", Home Care Surfactants, pp. 141-144, Oct. 2015.

(Continued)

*Primary Examiner* — Shirley V Gembeh
(74) *Attorney, Agent, or Firm* — McKee, Vorhees & Sease, PLLC

(57) ABSTRACT

Antimicrobial compositions including at least one acid and at least one anionic surfactant are provided. In particular, food contact antimicrobial compositions including at least one acid and at least one anionic surfactant provide a no-rinse compositions efficacious against Norovirus, having acceptable use solution pH that do not require use of personal protective equipment (PPE), are surface compatible and do not leave residues on treated surfaces are provided. Methods of cleaning a surface with the compositions are also provided.

19 Claims, 1 Drawing Sheet

(56) References Cited

U.S. PATENT DOCUMENTS

| | | |
|---|---|---|
| 6,699,825 B2 | 3/2004 | Rees et al. |
| 6,701,940 B2 | 3/2004 | Tsibouklis et al. |
| 6,740,626 B2 | 5/2004 | Neumiller |
| 6,794,346 B2 | 9/2004 | Wick et al. |
| 6,936,579 B2 | 8/2005 | Urban |
| 6,982,245 B1 | 1/2006 | Faubel et al. |
| 7,053,039 B2 | 5/2006 | Burt et al. |
| 7,196,046 B2 | 3/2007 | Cheung et al. |
| 7,304,022 B2 | 12/2007 | Cheung et al. |
| 7,488,708 B2 | 2/2009 | Deljosevic et al. |
| 7,569,232 B2 | 8/2009 | Man et al. |
| 7,569,530 B1 | 8/2009 | Pan et al. |
| 7,943,565 B2 | 5/2011 | Kany et al. |
| 7,998,919 B2 | 8/2011 | Rong et al. |
| 8,093,195 B2 | 1/2012 | Uhl et al. |
| 8,143,309 B2 | 3/2012 | Awad |
| 8,187,652 B2 † | 5/2012 | Man |
| 8,198,227 B2 | 6/2012 | Cermenati et al. |
| 8,268,334 B2 | 9/2012 | Dreilinger et al. |
| 8,282,743 B2 | 10/2012 | Bonnechere et al. |
| 8,410,038 B2 | 4/2013 | Davister et al. |
| 8,420,587 B2 | 4/2013 | Cermenati et al. |
| 8,563,496 B2 | 10/2013 | Cermenati et al. |
| 8,618,041 B2 | 12/2013 | Toussaint et al. |
| 8,722,609 B2 * | 5/2014 | Choczaj ............... C11D 3/3409 510/191 |
| 8,729,005 B2 | 5/2014 | McKechnie et al. |
| 9,096,821 B1 | 8/2015 | Hope et al. |
| 9,115,136 B2 | 8/2015 | Maeckawa et al. |
| 2001/0046979 A1 | 11/2001 | Roselle et al. |
| 2005/0065055 A1 | 3/2005 | Barnes |
| 2005/0121054 A1 | 6/2005 | Barnabas et al. |
| 2005/0239676 A1 | 10/2005 | Gaudreault |
| 2006/0035808 A1 | 2/2006 | Ahmed et al. |
| 2006/0100128 A1 | 5/2006 | McCue et al. |
| 2006/0194709 A1 | 8/2006 | Boone et al. |
| 2006/0293202 A1 | 12/2006 | Cate et al. |
| 2006/0293214 A1 | 12/2006 | Cheng et al. |
| 2007/0027119 A1 | 2/2007 | Ahmed et al. |
| 2008/0015134 A1 | 1/2008 | Ahmed et al. |
| 2008/0139443 A1 | 6/2008 | Buzinski et al. |
| 2008/0255023 A1 | 10/2008 | Shimmin et al. |
| 2009/0035339 A1 † | 2/2009 | Istvan |
| 2009/0197786 A1 | 8/2009 | Perry et al. |
| 2009/0312225 A1 | 12/2009 | Szewczyk et al. |
| 2009/0312226 A1 | 12/2009 | Szewczyk et al. |
| 2009/0312227 A1 | 12/2009 | Murphy et al. |
| 2010/0154823 A1 | 6/2010 | Cermenati et al. |
| 2010/0286014 A1 | 11/2010 | Barnes |
| 2011/0230385 A1 | 9/2011 | Murphy et al. |
| 2012/0121679 A1 | 5/2012 | Cannon et al. |
| 2012/0122756 A1 | 5/2012 | Gaudreault |
| 2012/0136051 A1 | 5/2012 | Li et al. |
| 2012/0142577 A1 | 6/2012 | Sun et al. |
| 2012/0225943 A1 | 9/2012 | Gohl et al. |
| 2012/0302642 A1 | 11/2012 | Post |
| 2013/0196890 A1 | 8/2013 | Post |
| 2013/0331308 A1 | 12/2013 | Rees et al. |
| 2014/0024572 A1 | 1/2014 | Gaudreault |
| 2014/0041686 A1 | 2/2014 | Ryther et al. |
| 2014/0066356 A1 | 3/2014 | Gaudreault |
| 2014/0275267 A1 | 9/2014 | Beug-Deeb et al. |
| 2015/0093425 A1 | 4/2015 | Moore |
| 2015/0225674 A1 | 8/2015 | Masters et al. |
| 2015/0335598 A1 † | 11/2015 | Buchalova |
| 2016/0100577 A1 | 4/2016 | Salminen et al. |
| 2016/0150779 A1 † | 6/2016 | Li |
| 2017/0015947 A1 | 1/2017 | Cermenati et al. |
| 2017/0173642 A1 | 6/2017 | Li et al. |
| 2017/0333586 A1 | 11/2017 | Kang et al. |
| 2018/0187129 A1 | 7/2018 | Traistaru et al. |
| 2018/0265808 A1 | 9/2018 | Gross |
| 2018/0303090 A1 | 10/2018 | Budhian et al. |
| 2019/0330568 A1 | 10/2019 | Ceulemans et al. |
| 2020/0140784 A1 | 5/2020 | Delaney et al. |

FOREIGN PATENT DOCUMENTS

| | | |
|---|---|---|
| CN | 104004598 A | 8/2014 |
| DE | 19804829 A1 | 8/1999 |
| EP | 0879276 B1 † | 7/1997 |
| EP | 1095663 A1 | 5/2001 |
| EP | 1447100 A1 | 8/2004 |
| EP | 2843034 A1 | 3/2015 |
| EP | 2965624 A1 | 1/2016 |
| EP | 2968631 * | 1/2016 |
| EP | 3228688 * | 11/2016 |
| IN | PCT200702696DEL P1 | 8/2007 |
| IN | 2736CHE2015 | 3/2016 |
| IN | 211DEL2015 | 7/2016 |
| JP | 58135802 A | 8/1983 |
| JP | H02308897 A | 12/1990 |
| JP | H04139202 A | 5/1992 |
| JP | H04332800 A | 11/1992 |
| JP | 6502868 A | 3/1994 |
| JP | 6507905 A | 9/1994 |
| JP | 8503209 A | 4/1996 |
| JP | 967599 A | 3/1997 |
| JP | 2000273494 A | 10/2000 |
| JP | 2002173698 A | 6/2002 |
| JP | 2003096498 A | 4/2003 |
| JP | 2003105386 A | 4/2003 |
| JP | 2004059806 A | 2/2004 |
| JP | 2008510033 A | 4/2008 |
| JP | 2008266375 A | 11/2008 |
| JP | 2010084087 A | 4/2010 |
| JP | 6165953 B1 | 7/2017 |
| KR | 101754451 B1 | 7/2017 |
| WO | 9320176 A1 | 10/1993 |
| WO | 9419443 A1 | 9/1994 |
| WO | 9504459 A1 | 2/1995 |
| WO | 9514070 A1 | 5/1995 |
| WO | 9609761 A1 | 4/1996 |
| WO | 9623605 A1 | 8/1996 |
| WO | 9715649 A1 | 5/1997 |
| WO | 9725403 A1 | 7/1997 |
| WO | 9801525 A2 | 1/1998 |
| WO | 9916854 A1 | 4/1999 |
| WO | 0063337 A1 | 10/2000 |
| WO | 0121753 A1 | 3/2001 |
| WO | 0164035 A2 | 9/2001 |
| WO | 0210325 A1 | 2/2002 |
| WO | 2005103218 A1 | 11/2005 |
| WO | 2008068154 A2 | 6/2008 |
| WO | 2009134706 A1 | 11/2009 |
| WO | 2015036433 A1 | 3/2015 |
| WO | 2015060775 A1 † | 4/2015 |
| WO | 2015120990 A1 | 8/2015 |
| WO | 2016124764 A1 | 8/2016 |
| WO | 2019103887 A1 | 5/2019 |

OTHER PUBLICATIONS

Ecolab USA Inc., "Annex to the invitation to pay additional fees", European Patent Office relating to PCT/US2018/052883 filed Sep. 26, 2018, dated Dec. 14, 2018.

International Searching Authority, PCT/US2018/052883, filing date Sep. 26, 2018, "Notification of Transmittal of the International Search Report and the Written Opinion of the International Searching Authority, or the Declaration", dated Feb. 5, 2019, 25 pages.

EPA, "Guidance to Registrants: Process for Making Claims Against Emerging Viral Pathogens not on EPA-Registered Disinfectant Lables", US Environmental Protection Agency, pp. 1-8, Aug. 19, 2016.

\* cited by examiner
† cited by third party

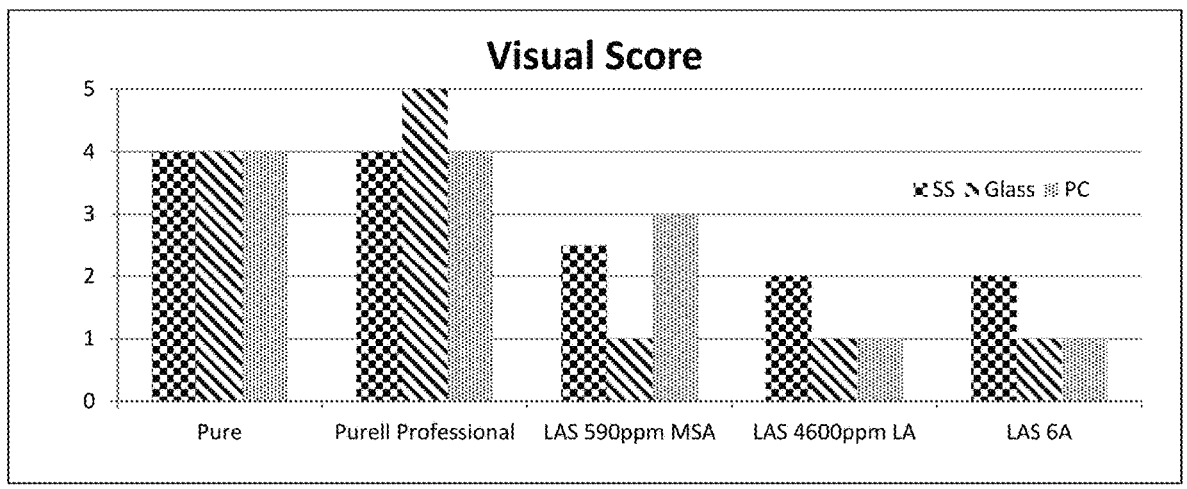

ACID/ANIONIC ANTIMICROBIAL AND VIRUCIDAL COMPOSITIONS AND USES THEREOF

CROSS-REFERENCE TO RELATED APPLICATIONS

This application claims priority under 35 U.S.C. § 119 to provisional application Ser. No. 62/563,461, filed Sep. 26, 2017, herein incorporated by reference in its entirety.

FIELD OF THE INVENTION

The invention relates to antimicrobial compositions including at least one acid and at least one anionic surfactant. In particular, food contact (or non-food contact) antimicrobial compositions including at least one acid and at least one anionic surfactant provide a no-rinse composition efficacious for sanitizing and against Norovirus, having acceptable use solution pH that do not require use of personal protective equipment (PPE), are surface compatible and do not result in streaky, hazy or tacky residues on treated surfaces. The compositions are suitable for use as hard surface antimicrobial compositions, including ware wash applications, $3^{rd}$ sink sanitizers, food contact and non-food contact applications, biofilm treatment compositions, among others, including those which are an alternative to quaternary ammonium compounds. Methods of cleaning a surface with the compositions are also provided.

BACKGROUND OF THE INVENTION

Microbial and Viral pathogens are an increasing public health concern. Pathogenic viruses present a significant health concern as they are able to persist on surfaces for longer periods of time and require complete and reliable inactivation in order to stop disease transmission. Viruses can be identified according to a hierarchy that correspondences with the level of resistance to being inactivated. The three viral subgroups include small non-enveloped, large non-enveloped, and enveloped viruses. An antimicrobial product that is able to inactivate a small, non-enveloped virus is also able to inactivate any large, non-enveloped virus or any enveloped virus. Similarly, an antimicrobial product that can inactivate a large, non-enveloped virus is also able to inactivate any enveloped virus. Accordingly it is desirable to identify and develop antimicrobial compositions that can inactivate small, non-enveloped viruses to then be able to have corresponding antimicrobial efficacy across the viral hierarchy. Norovirus is an exemplary small, non-enveloped virus in need of additional antimicrobial compositions for surface treatment.

Norovirus is an exemplary small, non-enveloped virus in need of additional antimicrobial compositions for surface treatment. The non-enveloped Norovirus (NoV), also known previously as "Norwalk-Like Virus" (NLV) or small round structured virus, is the most important viral pathogen of epidemic acute gastroenteritis that occurs in both developed and developing countries. NoV belongs to the Caliciviridae family and are icosahedral, single stranded, positive-sense RNA viruses whose capsids are composed of 180 copies of a single major structural protein. Noroviruses are estimated to cause 23 million cases of acute gastroenteritis in the United States per year, and are the leading cause of gastroenteritis in the United States. Of viruses, only the common cold is reported more often than viral gastroenteritis (norovirus). Norovirus causes nausea, vomiting (sometimes accompanied by diarrhea), and stomach cramps. This infection typically is spread from person to person by direct contact.

Noroviruses are very highly contagious and can spread easily from person to person. People can become infected with the norovirus in several ways, including, eating food or drinking liquids that are contaminated with norovirus; touching surfaces or objects contaminated with norovirus, and then placing their hands in their mouths; or having direct contact with another person who is infected and showing symptoms (for example, when caring for someone who is ill, or sharing foods or eating utensils with someone who is ill). During outbreaks of norovirus gastroenteritis, several modes of transmission have been documented, for example, initial foodborne transmission in a restaurant, followed by secondary person-to-person transmission to household contacts.

Quaternary ammonium compounds have become a commonplace antimicrobial and are widely used within the foodservice industry for food contact sanitizing and disinfectant applications with disinfection claim sets requiring a follow-up rinse step. However, recent regulatory scrutiny over quaternary ammonium compounds may change the utilization of these sanitizing and disinfectant compositions.

Quaternary ammonium compounds and other chemistries are utilized in products for treating Norovirus, which is a highly contagious, significant public health burden. Norovirus is one of the most difficult viruses to disinfect. Norovirus is the most common cause of epidemic gastroenteritis causing at least 50% of all outbreaks with an estimated 20 million cases in the U.S. each year and is the leading cause of foodborne illness. The financial impact is large. The cost per case of Norovirus is low relative to other foodborne illnesses but due to its high incidence the total cost of illness for Norovirus is substantial. Norovirus is sourced from the feces or vomit of an infected person and is spread through a number of ways including contact with unwashed hands, ingestion of contaminated food or water, and contact with contaminated surfaces. Studies have shown an infected person may be contagious for 2 weeks after recovery and may continue shedding virus particles in feces for as long as 2 months. Given the persistence of Norovirus, decontamination of surfaces should take place long after an infected person is no longer showing symptoms.

Products having a no-rinse capability are desirable, although they present challenges due to regulatory requirements for all active and inert ingredients to have a list tolerance designated for chemical substances used as ingredients in antimicrobial pesticide formulations applied to food-contact surfaces in public eating places, dairy-processing equipment, and food-processing equipment and utensils. Various commercially-available products exist in the marketplace that provide no-rinse options for Norovirus, including for example, Purell Professional Food Service Sanitizer as disclosed in U.S. Pat. No. 8,143,309 and Pure Bioscience Pure Hard Surface as disclosed in U.S. Pat. Nos. 6,197,814 and 6,583,176, the entire contents of which are incorporated by reference in their entirety. However, there are various challenges presented by the products. For example, various products present flammability concerns, impart hazy and/or tacky residues and/or poor surface appearance, having limited compatibility with soft metal surfaces (including aluminum) and are only available as ready-to-use (RTU) formulations instead of concentrates and/or solids, which limits applications of their use. As a result, there are various limitations which set in place a need for improved compositions.

Accordingly, it is an objective of the compositions and methods to provide a product that can offer no-rinse disinfection without the use of quaternary ammonium compounds.

A further object of the compositions and methods is to provide antimicrobial and disinfectant compositions against Norovirus (and other small, non-enveloped viruses to also provide antiviral efficacy against large, non-eveloped viruses and enveloped viruses), including short contact time, preferably 10 minutes or less, more preferably 5 minutes or less, and most preferred 1 minute or less.

A further object of the compositions and methods is a treatment option providing acceptable material compatibility that supports good cleaning performance without a hazy, streaky, or tacky residue on the treated surface.

A further object of the compositions and methods is a treatment option having a use solution pH that does not require the use of personal protective equipment (PPE).

A still further object of the compositions and methods is to provide efficacy against biofilms.

Other objects, advantages and features of the present invention will become apparent from the following specification taken in conjunction with the accompanying drawings.

BRIEF SUMMARY OF THE INVENTION

An advantage of the compositions and methods is that antimicrobial compositions provide dilutable, non-flammable, no-rinse efficacy against microbial pathogens, including viruses such as Norovirus, while providing surface compatible formulations that do not leave hazy, streaky, or tacky residues on treated surfaces. It is a further advantage of the compositions and methods that use solution pH do not require a user to employ PPE. As still further benefits, the compositions are suitable for use as hard surface antimicrobial compositions, including ware wash applications, $3^{rd}$ sink sanitizers, food contact and non-food contact applications, biofilm treatment compositions, among others, including those which are an alternative to quaternary ammonium compounds.

In an embodiment, an antimicrobial composition comprises from about 10 wt-% to about 75 wt-% of at least one acid, wherein the acid is a strong acid, weak acid and/or combination thereof; at least one sulfonate, sulfate and/or carboxylate anionic surfactant; and water, wherein the composition is a dilutable liquid concentrate having an acidic pH that is non-flammable. In a further embodiment, the anionic surfactant is a C8-C22 alkyl sulfonate, and/or alpha sulfonated carboxylic acid or its ester, preferably linear alkyl benzene sulfonic acid. In a further embodiment the acids comprise lactic acid and methane sulfonic acid. In further embodiments, the compositions also include an alkoxylated nonionic surfactant having an EO/PO block copolymer. A use solution of the compositions have a pH from about 1.5 to about 4. In further embodiments, the liquid compositions can be saturated onto a wipe substrate. In still further embodiments the liquid compositions can be provided as a ready to use composition comprising from about 5 ppm to about 10,000 pm of the at least one acid and from about 10 ppm to about 6,000 ppm of the anionic surfactant.

In further embodiments, methods of using an antimicrobial composition, comprise: contacting the antimicrobial composition of claim 1 to a surface in need of treatment; wherein the method does not require a rinse step and achieves at least a 3-log microbial reduction. In embodiments, the contacting is by wiping, dipping, immersing, or spraying, and wherein the surface is a hard surface, a precleaned hard surface, a surface contaminated with Norovirus and/or biofilm, and/or a human or mammalian tissue. In embodiments, the contacting provides complete kill of the Norovirus in less than 1 minute, and wherein the contacting step is at an aqueous use temperature from about 40° F.-160° F. In embodiments, the concentrate is diluted at a rate of from about ⅛ oz./gal. to about 2 oz./gal. to form a use solution comprising from about 5 ppm to about 10,000 ppm of at least one acid, and from about 10 ppm to about 6000 ppm of at least one anionic surfactant, and wherein the use solution pH from about 1.5 to about 4.

In an embodiment, a virucidal composition comprises from about 10 wt-% to about 75 wt-% of at least one strong acid and at least one weak acid; at least one sulfonate, sulfate and/or carboxylate anionic surfactant; and water, wherein the composition is a dilutable acidic liquid concentrate that is non-flammable, wherein a use pH of the composition is from about 1.5 to about 4. In still further embodiments, the composition of claim 16, wherein the anionic surfactant is a C8-C22 alkyl sulfonate and/or alpha sulfonated carboxylic acid or its ester, and wherein the weak acid comprises from about 10 wt-% to about 50 wt-% and the strong acid comprises from about 0.1 wt-% to about 19 wt-%, and the at least one anionic surfactant comprises from about 0.2 wt-% to about 50 wt-%.

In further embodiments, methods of inactivating a virus include: contacting the virucidal composition of claim 16 to a surface in need of treatment; wherein the contacting provides antiviral inactivation efficacy from at least a 3 log reduction to complete inactivation within less 1 minute, or preferably less than 30 seconds, and wherein the method does not require a rinse step and does not impart a residue on the treated surface. In embodiments of the methods, the virus is a small, non-enveloped virus, a large, non-enveloped virus, and/or an enveloped virus. In preferred embodiments, the virus is Norovirus.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1 shows cleaning performance evaluation results comparing commercially-available products with efficacy against Norovirus compared to the acid/anionic surfactant compositions disclosed herein.

Various embodiments of the present invention will be described in detail with reference to the drawings, wherein like reference numerals represent like parts throughout the several views. Reference to various embodiments does not limit the scope of the invention. FIGURES represented herein are not limitations to the various embodiments according to the invention and are presented for exemplary illustration of the invention.

DETAILED DESCRIPTION OF THE PREFERRED EMBODIMENT

The present invention relates to dilutable, non-flammable antimicrobial compositions providing no-rinse efficacy against microbial and viral pathogens, including Norovirus, while providing surface compatible formulations that do not leave hazy, streaky, or tacky residues on treated surfaces and do not require PPE. The embodiments are not limited to particular compositions and methods of use thereof, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As referred to herein, antimicrobial compositions are further suitable for cidal activity against viral pathogens, including for example, Norovirus. For the purpose of this patent application, successful virucidal reduction is achieved when the viral populations are completely inactivated.

The term "biofilm," as used herein, means an extracellular matrix in which a population of microorganisms are dispersed and/or form colonies. Biofilms are understood to be typically made of polysaccharides and other macromolecules, often referred to as exopolysaccharides, that are concentrated at an interface (usually solid/liquid) and act as a binding agent that surrounds such populations of microorganisms. Biofilms are further understood to include complex associations of cells, extracellular products and detritus (or non-living particulate organic material) that are trapped within the biofilm or released from cells within the biofilm. The term biofilm, as used herein, further refers to the ASTM definition of biofilm as an accumulation of bacterial cells immobilized on a substratum and embedded in an organic polymer matrix of microbial origin. Biofilms are understood to be a dynamic, self-organized accumulation of microorganisms and microbial and environmental by-products that is determined by the environment in which it lives.

As used herein, the term "cleaning" refers to a method used to facilitate or aid in soil removal, bleaching, microbial population reduction, rinsing, and any combination thereof.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

The term "commercially acceptable cleaning performance" refers generally to the degree of cleanliness, extent of effort, or both that a typical consumer would expect to achieve or expend when using a cleaning product or cleaning system to address a typical soiling condition on a typical substrate. This degree of cleanliness may, depending on the particular cleaning product and particular substrate, correspond to a general absence of visible soils, or to some lesser degree of cleanliness. Cleanliness may be evaluated in a variety of ways depending on the particular cleaning product being used (e.g., ware or laundry detergent, rinse aid, hard surface cleaner, vehicular wash or rinse agent, or the like) and the particular hard or soft surface being cleaned (e.g., ware, laundry, fabrics, vehicles, and the like), and normally may be determined using generally agreed industry standard tests or localized variations of such tests. In the absence of such agreed industry standard tests, cleanliness may be evaluated using the test or tests already employed by a manufacturer or seller to evaluate the cleaning performance of its phosphorus-containing cleaning products sold in association with its brand. In some aspects, the methods provide commercially acceptable cleaning performance while ensuring the formulations do not leave hazy, streaky, or tacky residues on treated surfaces.

As used herein, the term "corrosive" refers to an agent or composition that results in chemical attack, oxidation, discoloration, dimensional changes and/or weight loss of a surface and/or pitting of a surface. Various mechanisms of corrosion are disclosed in Corrosion Basics, National Association of Corrosion Engineers, 1984, including for example, metal corrosion through a redox attack, attacking and penetrating the passivation layers of metal, pitting of surfaces, etc. Compositions that are non-corrosive beneficially do not cause or exhibit any chemical attack, oxidation, discoloration, dimensional and/or weight loss of a surface and/or pitting of a surface. Exemplary methodology for assessing corrosive or non-corrosive properties of a composition are illustrated in the Examples and can include weight assessment to measure surface changes and/or gloss measurements.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

The term "improved cleaning performance" refers generally to achievement by a substitute cleaning product or substitute cleaning system of a generally greater degree of cleanliness or with generally a reduced expenditure of effort, or both, when using the substitute cleaning product or substitute cleaning system rather than the conventional cleaning product to address a typical soiling condition on a typical substrate. This degree of cleanliness may, depending on the particular cleaning product and particular substrate, correspond to a general absence of visible soils, along with treated surfaces that do not have hazy, streaky, or tacky residues.

The terms "include" and "including" when used in reference to a list of materials refer to but are not limited to the materials so listed.

As used herein, the term "instrument" refers to the various medical or dental instruments or devices that can benefit from cleaning with a composition according to the present invention.

As used herein, the term "virucidal" refers to an agent that reduces the number of viruses on a surface or substrate. In an embodiment, virucidal compositions will provide at least a 3-log order reduction, or preferably a 5-log order reduction, or more preferably a complete inactivation of viruses. These reductions can be evaluated using a procedure set out in ASTM E1053 Standard Test Method for Efficacy of Virucidal Agents Intended for Inanimate Environmental Surfaces; US standards are set forth in EPA 810.2200. According to this reference a virucidal composition should provide a 99.9% reduction (3-log order reduction) for virucidal activity.

The term "virus", as used herein refers to a type of microorganism that can include both pathogenic and non-pathogenic viruses. Pathogenic viruses can be classified into two general types with respect to the viral structure: enveloped viruses and non-enveloped viruses. Some well-known enveloped viruses include herpes virus, influenza virus; paramyxovirus, respiratory syncytial virus, corona virus, HIV, hepatitis B virus, hepatitis C virus and SARS-CoV virus. Non-enveloped viruses, sometimes referred to as "naked" viruses, include the families Picornaviridae, Reoviridae, Caliciviridae, Adenoviridae and Parvoviridae. Members of these families include rhinovirus, poliovirus, adenovirus, hepatitis A virus, norovirus, papillomavirus, and rotavirus. It is known in the art that "enveloped" viruses are relatively sensitive and, thus, can be inactivated by commonly used disinfectants. In contrast, non-enveloped viruses are substantially more resistant to conventional disinfectants and are significantly more environmentally stable than enveloped viruses.

As used herein, the term "sanitizer" refers to an agent that reduces the number of bacterial contaminants to safe levels as judged by public health requirements. In an embodiment, sanitizers for use in this invention will provide at least a 3-log reduction and more preferably a 5-log order reduction. These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "soil" refers to polar or non-polar organic or inorganic substances including, but not limited to carbohydrates, proteins, fats, oils and the like. These substances may be present in their organic state or complexed to a metal to form an inorganic complex.

As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "threshold agent" refers to a compound that inhibits crystallization of water hardness ions from solution, but that need not form a specific complex with the water hardness ion. Threshold agents include but are not limited to a polyacrylate, a polymethacrylate, an olefin/maleic copolymer, and the like.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. The term "ware" generally refers to items such as eating and cooking utensils, dishes, and other hard surfaces. Ware also refers to items made of various substrates, including glass, ceramic, china, crystal, metal, plastic or natural substances such, but not limited to clay, bamboo, hemp and the like. Types of metals that can be cleaned with the compositions include but are not limited to, those that include aluminum, copper, brass, and stainless steel. Types of plastics that can be cleaned with the compositions include but are not limited to, those that include polypropylene (PP), high density polyethylene (HDPE), low density polyethylene (LDPE), polyvinyl chloride (PVC), syrene acrylonitrile (SAN), polycarbonate (PC), melamine formaldehyde resins or melamine resin (melamine), acrilonitrile-butadiene-styrene (ABS), and polysulfone (PS). Other exemplary plastics that can be cleaned using the compounds and compositions include polyethylene terephthalate (PET) polystyrene polyamide.

As used herein, the term "waters" includes food process or transport waters. Water temperatures can range from about 40° F.-160° F., about 60° F.-140° F., or about 70° F.-140° F. Food process or transport waters include produce transport waters (e.g., as found in flumes, pipe transports, cutters, slicers, blanchers, retort systems, washers, and the like), belt sprays for food transport lines, boot and handwash dip-pans, third-sink rinse waters, and the like. Waters also include domestic and recreational waters such as pools, spas, recreational flumes and water slides, fountains, and the like.

The term "water soluble" refers to a compound that can be dissolved in water at a concentration of more than 1 wt. %. The terms "sparingly soluble" or "sparingly water soluble" refer to a compound that can be dissolved in water only to a concentration of 0.1 to 1.0 wt. %. The term "water insoluble" refers to a compound that can be dissolved in water only to a concentration of less than 0.1 wt. %.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

Acid/Anionic Compositions

Exemplary ranges of the antimicrobial compositions and virucidal compositions are shown in Tables 1 and 2 showing liquid and solid formulations on an active concentration basis (Tables 1A and 1B) and weight percentage basis (Table 2A and 2B). Tables 1A-1B can include formulations with a minimum acid component and deionized water to provide required acidic pH for a ready to use formulation. The % by weight Tables 2A and 2B are shown at a 2 oz./gal dilutable liquid formulation, incorporating the range of actives outlined in Tables 1A and 1B. When converting concentration basis to weight percentage all raw materials were assumed 100% active. The 2 oz./gal dilution rate provides sufficient formulation space to formulate raw material to deliver up to 6000 ppm of any one raw material in a use solution.

Tables 2C and 2D are shown at a 0.25-1 oz./gal dilutable liquid formulation. Tables 2E and 2F show liquid concentrate formulations. Tables 2G and 2H show ready to use liquid formulations.

Tables 1B, 2B, 2D and 2H showing ranges for both the strong acid and weak acid with a lower threshold of 0%-wt indicate that either of the acids can be included in the formulation or a combination thereof. However, within the scope of the disclosure herein at least one acid is included in the formulation. In exemplary embodiments, for a 2 oz./gal dilutable formulation including only a strong acid would require at least about 0.1 wt-%, whereas a 0.25-1 oz./gal dilutable formulation including only a strong acid would require at least about 0.3 wt-% strong acid. In an exemplary embodiment, for a 2 oz./gal dilutable formulation including only a weak acid would require at least about 0.1 wt-%, whereas a 0.25-1 oz./gal dilutable formulation including only a weak acid would require at least about 0.8 wt-% weak acid. One skilled in the art can adjust % by weight of the compositions to arrive at a composition having a different dilution rate, which is within the scope of the disclosed compositions. Beneficially, within the ranges of actives, the compositions can be formulated to include a nearly or completely waterless liquid or solid composition.

TABLE 1A

| Material | First Exemplary Range ppm | Second Exemplary Range ppm | Third Exemplary Range ppm | Fourth Exemplary Range ppm |
| --- | --- | --- | --- | --- |
| Acid | 5-6000 | 150-5000 | 225-4500 | 300-4000 |
| Anionic Surfactant | 10-6000 | 50-4000 | 75-2000 | 100-1000 |
| Water | — | — | — | — |
| Additional Functional Ingredients (e.g. nonionic surfactant) | 0-6000 | 0-3000 | 0-2000 | 0-1000 |

TABLE 1B

| Material | First Exemplary Range ppm | Second Exemplary Range ppm | Third Exemplary Range ppm | Fourth Exemplary Range ppm |
| --- | --- | --- | --- | --- |
| Strong Acid | 0-3000 | 0-2000 | 0-1000 | 0-10000 |
| Weak Acid | 0-6000 | 0-5000 | 0-4500 | 0-4000 |
| Anionic Surfactant | 10-6000 | 50-4000 | 75-2000 | 100-1000 |
| Water | — | — | — | — |
| Additional Functional Ingredients (e.g. nonionic surfactant) | 0-6000 | 0-3000 | 0-2000 | 0-1000 |

TABLE 2A

| Material | First Exemplary Range wt-% | Second Exemplary Range wt-% | Third Exemplary Range wt-% | Fourth Exemplary Range wt-% |
| --- | --- | --- | --- | --- |
| Acid | 0.1-38 | 1-32 | 1.5-29 | 2-26 |
| Anionic Surfactant | 0.1-38 | 0.3-26 | 0.5-13 | 0.6-6.4 |
| Water | to 100% | to 100% | to 100% | to 100% |
| Additional Functional Ingredients (e.g. nonionic surfactant) | 0-38% | 0-19% | 0-13% | 0-6% |

TABLE 2B

| Material | First Exemplary Range wt-% | Second Exemplary Range wt-% | Third Exemplary Range wt-% | Fourth Exemplary Range wt-% |
| --- | --- | --- | --- | --- |
| Strong Acid | 0-19 | 0-13 | 0-6 | 0-6 |
| Weak Acid | 0-38 | 0-32 | 0-29 | 0-26 |
| Anionic Surfactant | 0.1-38 | 0.3-26 | 0.5-13 | 0.6-6.4 |
| Water | to 100 | to 100 | to 100 | to 100 |
| Additional Functional Ingredients (e.g. nonionic surfactant) | 0-38 | 0-19 | 0-13 | 0-6 |

TABLE 2C

| Material | First Exemplary Range wt-% | Second Exemplary Range wt-% | Third Exemplary Range wt-% | Fourth Exemplary Range wt-% |
| --- | --- | --- | --- | --- |
| Acid | 0.3-95 | 5-80 | 10-70 | 30-60 |
| Anionic Surfactant | 0.5-50 | 2.5-40 | 3.75-35 | 5-25 |
| Water | to 100% | to 100% | to 100% | to 100% |
| Additional Functional Ingredients (e.g. nonionic surfactant) | 0-75 | 0-50 | 0-40 | 0-25 |

TABLE 2D

| Material | First Exemplary Range wt-% | Second Exemplary Range wt-% | Third Exemplary Range wt-% | Fourth Exemplary Range wt-% |
| --- | --- | --- | --- | --- |
| Strong Acid | 0-75 | 0-50 | 0-25 | 0-15 |
| Weak Acid | 0-95 | 0-80 | 0-70 | 60 |
| Anionic Surfactant | .5-50 | 2.5-40 | 3.75-35 | 5-25 |
| Water | to 100% | to 100% | to 100% | to 100% |
| Additional Functional Ingredients (e.g. nonionic surfactant) | 0-75 | 0-50 | 0-40 | 0-25 |

TABLE 2E

| Material | First Exemplary Range wt-% | Second Exemplary Range wt-% | Third Exemplary Range wt-% | Fourth Exemplary Range wt-% |
| --- | --- | --- | --- | --- |
| Acid | 10-75 | 10-70 | 20-70 | 30-60 |
| Anionic Surfactant | 1-40 | 1-30 | 2-30 | 5-20 |
| Water | to 100 | to 100 | to 100 | to 100 |
| Additional Functional Ingredients (e.g. nonionic surfactant) | 0-75 | 0-50 | 0-40 | 0-25 |

TABLE 2F

| Material | First Exemplary Range wt-% | Second Exemplary Range wt-% | Third Exemplary Range wt-% | Fourth Exemplary Range wt-% |
| --- | --- | --- | --- | --- |
| Weak Acid | 8-55 | 10-50 | 10-50 | 20-45 |
| Strong Acid | 2-20 | 4-20 | 5-20 | 8-20 |
| Anionic Surfactant | 1-40 | 1-30 | 2-30 | 5-20 |
| Nonionic Surfactant | 0-20 | 0-15 | 0.1-15 | 1-10 |
| Water | to 100 | to 100 | to 100 | to 100 |
| Additional Functional Ingredients (e.g. nonionic surfactant) | 0-75 | 0-50 | 0-40 | 0-25 |

TABLE 2G

| Material | First Exemplary Range ppm | Second Exemplary Range ppm | Third Exemplary Range ppm | Fourth Exemplary Range ppm |
| --- | --- | --- | --- | --- |
| Acid | 5-10,000 | 50-5000 | 50-4000 | 50-2000 |
| Anionic Surfactant | 10-6000 | 50-4000 | 75-2000 | 100-1000 |
| Water and additional functional ingredients | Added to 100% | Added to 100% | Added to 100% | Added to 100% |

TABLE 2H

| Material | First Exemplary Range ppm | Second Exemplary Range ppm | Third Exemplary Range ppm | Fourth Exemplary Range ppm |
| --- | --- | --- | --- | --- |
| Strong Acid | 0-3000 | 0-2000 | 0-1000 | 0-1000 |
| Weak Acid | 0-10,000 | 0-5000 | 0-4000 | 0-2000 |
| Anionic Surfactant | 10-6000 | 50-4000 | 75-2000 | 100-1000 |
| Water and additional functional ingredients | Added to 100% | Added to 100% | Added to 100% | Added to 100% |

The antimicrobial compositions and virucidal compositions may include concentrate compositions which can be diluted to form use compositions or ready to use (RTU) compositions. Beneficially, the compositions overcome a limitation of the prior art in that dilutable concentrates can be provided. In general, a concentrate refers to a composition that is intended to be diluted with water to provide a use solution that contacts an object to provide the desired cleaning, antimicrobial efficacy, or the like. The antimicrobial composition and virucidal composition that contacts the articles can be referred to as a concentrate or a use composition (or use solution) dependent upon the formulation employed in the methods described herein. It should be understood that the concentration of the acids, anionic surfactant(s), and any additional functional ingredients, such as nonionic surfactants, in the composition will vary depending on whether the composition is provided as a concentrate or as a use solution.

A use solution may be prepared from the concentrate by diluting the concentrate with water at a dilution ratio that provides a use solution having desired detersive properties. The water that is used to dilute the concentrate to form the use composition can be referred to as water of dilution or a diluent, and can vary from one location to another. The typical dilution factor is between approximately 1 and approximately 10,000. In an embodiment, the concentrate is diluted at a ratio of between about 1:10 and about 1:10,000 concentrate to water, between about 1:10 and about 1:1,000 concentrate to water, or between about 1:10 and about 1:510 concentrate to water.

In another aspect, a concentrate can be diluted at a rate of from about ⅛ oz./gal. to about 2 oz./gal., from about ¼ oz./gal. to about 1 oz./gal., or from about ½ oz./gal. to about 1 oz./gal while providing food contact sanitizing efficacy. In an aspect, the dilutable concentrate compositions provide a use solution pH from about 1.5 to about 4, from about 2 to about 4, from about 2.2 to about 3.5, or from about 2.5 to about 3.5, including a ranges therebetween.

The liquid compositions can be provided in various forms well appreciated by those skilled in the art. The compositions can also be manufactured to include a saturated antimicrobial wipe, such as a paper or cloth substrate having the liquid compositions saturated thereon.

The solid compositions can be provided in various forms well appreciated by those skilled in the art. The compositions can be manufactured to include a solid block, including pressed solid, cast solid, or the like. Various forms and sizes of the solids can be included in addition to solid blocks, including for example, pucks, tablets, powders, and the like.

Acid

The compositions include at least one acid. In embodiments, the compositions include two acids. In such an aspect, the acids can be a combination of a weak acid and a strong acid. For the purposes of this invention, an acid is a component that can be added to an aqueous system and result in a pH less than 7. Strong acids that can be used are acids which substantially dissociate an aqueous solution. "Weak" organic and inorganic acids are acids or acid components in which the first dissociation step of a proton from the acid moiety does not proceed essentially to completion when the acid is dissolved in water at ambient temperatures at a concentration within the range useful to form the present compositions.

Without wishing to be bound by theory, the acids of the compositions serve to protonate the carboxylate functionalities on the phospholipid membrane of bacteria and reduce the tendency of the membrane to electronically repel anionic surfactants included in the antimicrobial compositions and virucidal compositions. With respect to viruses, the acids are believed to affect the lipid envelope and/or capsid in the same manner. Moreover, the acids disclosed herein facilitate the creation of a low pH buffer on the surface of a substrate, thereby prolonging the residual antimicrobial and virucidal activity of the compositions and products in which they are incorporated.

Exemplary strong acids suitable for use in the compositions include methane sulfonic acid, sulfuric acid, sodium hydrogen sulfate, phosphoric acid, phosphonic acid, nitric acid, sulfamic acid, hydrochloric acid, trichloroacetic acid, trifluoroacetic acid, toluene sulfonic acid, glutamic acid, and the like; alkane sulfonic acid, such as methane sulfonic acid, ethane sulfonic acid, linear alkyl benzene sulfonic acid, xylene sulfonic acid, cumene sulfonic acid and the like. In a preferred aspect, the compositions include a strong acid having a pKa less than about 2.5 to beneficially provide the acidic use compositions having a pH less than about 4, or preferably less than about 3. In an embodiment, the compositions include a strong acid in combination with the anionic surfactant, and optionally include a weak acid.

Exemplary weak acids suitable for use in the compositions including alpha hydroxycarboxylic acid, such as lactic acid, citric acid, tartaric acid, malic acid, gluconic acid, and the like; carboxylic acids, such as formic acid, acetic acid, propionic acid and the like; other common organic acids such as ascorbic acid, glutamic acid, levulinic acid, etc. could also be used. In a preferred aspect, the compositions include a weak acid having a pKa greater than about 2.5 to beneficially provide the acidic use compositions having a pH less than about 4, or preferably less than about 3. In an embodiment, the compositions include a weak acid in combination with the anionic surfactant, and optionally include a strong acid.

In some embodiments, the compositions do not include fatty acids.

In certain embodiments, a combination of a strong acid with a weak acid result in surprisingly increased antimicrobial and virucidal efficiency. In a preferred embodiment, the acids comprise lactic acid and methane sulfonic acid. Without being limited to a particular mechanism of action, it may be desirable to have a buffered acidic composition. For example, if a surface in need of treatment is not sufficiently cleaned the compositions have a buffered composition by virtue of a combination of weak and strong acids will beneficially be able to support inactivation of pH sensitive organisms.

In an aspect, the compositions having about a 2 oz./gal dilution include from about 0.1 wt-% to about 50 wt-% of at least one acid, from about 0.1 wt-% to about 38 wt-% of at least one acid, from about 1 wt-% to about 32 wt-% of at least one acid, from about 1.5 wt-% to about 29 wt-% of at least one acid, or from about 2 wt-% to about 26 wt-% of at least one acid, in addition to the ranges set forth in Tables above. In addition, without being limited according to the invention, all ranges recited are inclusive of the numbers defining the range and include each integer within the defined range.

In an aspect, the compositions having about a 0.25-1 oz./gal dilution include from about 0.3 wt-% to about 95 wt-% of at least one acid, from about 1 wt-% to about 90 wt-% of at least one acid, from about 5 wt-% to about 80 wt-% of at least one acid, from about 10 wt-% to about 70 wt-% of at least one acid, or from about 30 wt-% to about 60 wt-% of at least one acid, in addition to the ranges set forth in Tables above. In addition, without being limited according to the invention, all ranges recited are inclusive of the numbers defining the range and include each integer within the defined range.

In certain aspect, the compositions having about a 2 oz./gal dilution include from about 0.1 wt-% to about 20 wt-% of a strong acid, from about 0.1 wt-% to about 19 wt-% of a strong acid, from about 0.1 wt-% to about 13 wt-% of a strong acid, or from about 0.1 wt-% to about 6 wt-% of a strong acid, in combination with a weak acid, wherein the compositions include from about 0.1 wt-% to about 40 wt-% of a weak acid, from about 0.1 wt-% to about 38 wt-% of a weak acid, from about 0.1 wt-% to about 32 wt-% of a weak acid, from about 0.1 wt-% to about 29 wt-% of a weak acid, or from about 0.1 wt-% to about 26 wt-% of a weak acid, in addition to the ranges set forth in Tables above. In addition, without being limited according to the invention, all ranges recited are inclusive of the numbers defining the range and include each integer within the defined range.

In certain aspect, the compositions having about a 0.25-1 oz./gal dilution include from about 0.1 wt-% to about 75 wt-% of a strong acid, from about 0.1 wt-% to about 75 wt-% of a strong acid, from about 0.1 wt-% to about 50 wt-% of a strong acid, from about 0.1 wt-% to about 25 wt-% of a strong acid, or from about 0.1 wt-% to about 15 wt-% of a strong acid, in combination with a weak acid, wherein the compositions include from about 0.1 wt-% to about 95 wt-% of a weak acid, from about 0.1 wt-% to about 80 wt-% of a weak acid, from about 0.1 wt-% to about 70 wt-% of a weak acid, or from about 0.1 wt-% to about 60 wt-% of a weak acid, in addition to the ranges set forth in Tables above. In addition, without being limited according to the invention, all ranges recited are inclusive of the numbers defining the range and include each integer within the defined range.

In certain aspects, the compositions before any dilution include from about 10 wt-% to about 75 wt-% acids (including strong and/or weak acids), from about 15 wt-% to about 75 wt-% acids, from about 20 wt-% to about 75 wt-% acids, from about 30 wt-% to about 75 wt-% acids, from about 30 wt-% to about 70 wt-% acids, from about 40 wt-% to about 70 wt-% acids, or from about 40 wt-% to about 60 wt-% acids. In addition, without being limited according to the invention, all ranges recited are inclusive of the numbers defining the range and include each integer within the defined range. In certain aspects, the compositions at a ready to use concentration include from about 5 ppm to about 10,000 ppm acids (including strong and/or weak acids), from about 50 ppm to about 5,000 ppm acids, 50 ppm to about 4,000 ppm acids, or from about 50 ppm to about 2,000 ppm acids.

In certain aspects, the compositions at a ready to use concentration include from about 0 ppm to about 3,000 ppm strong acid, from about 0 ppm to about 2,000 ppm strong acid, 0 ppm to about 1,000 ppm strong acid, or from about 0 ppm to about 1,000 ppm strong acid. In certain aspects, the compositions at a ready to use concentration include from about 0 ppm to about 10,000 ppm weak acid, from about 0 ppm to about 5,000 ppm weak acid, 0 ppm to about 4,000 ppm weak acid, or from about 0 ppm to about 2,000 ppm weak acid. In addition, without being limited according to the invention, all ranges recited are inclusive of the numbers defining the range and include each integer within the defined range.

Anionic Surfactants

The compositions include at least one anionic surfactant. In embodiments, the compositions include two anionic surfactants. In embodiments, the compositions include more than two anionic surfactants. Anionic surfactants are surface active substances which are categorized by the negative charge on the hydrophobe; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counter ions) associated with these polar groups, sodium, lithium and potassium impart water solubility; ammonium and substituted ammonium ions provide both water and oil solubility; and, calcium, barium, and magnesium promote oil solubility.

Anionic sulfonate surfactants suitable for use in the compositions also include alkyl sulfonates, the linear and branched primary and secondary alkyl sulfonates, and the aromatic sulfonates with or without substituents. In an aspect, sulfonates include sulfonated carboxylic acid esters.

In an aspect, suitable alkyl sulfonate surfactants include C8-C22 alkyl sulfonates, or preferably C10-C22 alkyl sulfonates. In an exemplary aspect, the anionic alkyl sulfonate surfactant is linear alkyl benzene sulfonic acid (LAS). In a preferred embodiment employing LAS as the anionic surfactant, the compositions are most effective at pH 3.0 or below.

Anionic sulfate surfactants suitable for use in the compositions also include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Additional anionic surfactants suitable for the compositions include anionic carboxylate surfactants, those which have a carboxylic acid or an alpha hydroxyl acid group. Anionic carboxylate surfactants suitable for use in the compositions also include carboxylic acids (and salts), such as alkanoic acids (and alkanoates), ester carboxylic acids (including sulfonated carboxylic acid esters), ether carboxylic acids, sulfonated fatty acids, such as sulfonated oleic acid, and the like. In an aspect, suitable ester carboxylic acids include alkyl succinates, such as for example dioctyl sulfosuccinate. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

$$R-O-(CH_2CH_2O)_n(CH_2)_m-CO_2X \quad (3)$$

in which R is a $C_8$ to $C_{22}$ alkyl group or

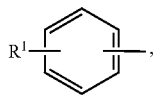, in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

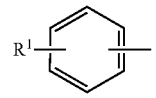

and $R^1$ is a $C_6$-$C_{12}$ alkyl group. In still yet other embodiments, $R^1$ is a $C_9$ alkyl group, n is 10 and m is 1.

Another class of anionic surfactant include the alpha sulfonated carboxylic acid esters, such as MC or PC-48 from Stepan.

In a preferred embodiment, the anionic surfactant does not include a sulfonate surfactant.

In an aspect, the compositions having about a 2 oz./gal dilution include from about 0.1 wt-% to about 40 wt-% of at least one anionic surfactant, from about 0.1 wt-% to about 38 wt-% of at least one anionic surfactant, from about 0.3 wt-% to about 26 wt-% of at least one anionic surfactant, from about 0.5 wt-% to about 13 wt-% of at least one anionic surfactant, or from about 0.6 wt-% to about 6.4 wt-% of at least one anionic surfactant. In addition, without being limited according to the invention, all ranges recited are inclusive of the numbers defining the range and include each integer within the defined range.

In an aspect, the compositions having about a 0.25-1 oz./gal dilution include from about 0.2 wt-% to about 50 wt-% of at least one anionic surfactant, from about 1 wt-% to about 40 wt-% of at least one anionic surfactant, from about 2 wt-% to about 30 wt-% of at least one anionic surfactant, or from about 2.5 wt-% to about 25 wt-% of at least one anionic surfactant. In addition, without being limited according to the invention, all ranges recited are inclusive of the numbers defining the range and include each integer within the defined range.

Additional Functional Ingredients

The components of the antimicrobial compositions and virucidal compositions can further be combined with various additional functional components. In some embodiments, the antimicrobial composition and virucidal composition including the at least one acid and at least one anionic surfactant make up a large amount, or even substantially all of the total weight of the composition. For example, in some embodiments few or no additional functional ingredients are included therein.

In other embodiments, additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used.

In preferred embodiments, the compositions do not include quaternary ammonium compounds. In additional embodiments, the compositions do not include conventional Norovirus actives, including for example, ethanol, silver citrate, and/or electrolytic chlorine. In additional embodiments the compositions do not include alcohols and/or other organic solvents to beneficially provide a non-flammable product. In other embodiments, the compositions may include solidifying agents, defoaming agents, wetting agents, anti-redeposition agents, solubility modifiers, dispersants, rinse aids, metal protecting agents, stabilizing agents, corrosion inhibitors, sequestrants and/or chelating agents, threshold agent, fragrances and/or dyes, rheology modifiers or thickeners, hydrotropes or couplers, buffers, solvents, sensor indicators, and the like.

Surfactants

In some embodiments, the compositions include an additional surfactant. Surfactants suitable for use with the compositions include, but are not limited to, nonionic surfactants, amphoteric surfactants, and/or zwitterionic surfactants. In some embodiments, the compositions include about 0 wt-% to about 40 wt-%, between about 0.1 wt-% to about 38 wt-%, between about 1 wt-% to about 20 wt-%, between about 1 wt-% to about 15 wt-% additional surfactant, or between about 1 wt-% to about 6 wt-% additional surfactant.

Nonionic Surfactants

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-(EO)$_5$(PO)$_4$) and Dehypon LS-36 (R-(EO)$_3$(PO)$_6$); and capped alcohol alkoxylates, such as Plurafac LF221 and Tegoten EC11; mixtures thereof, or the like.

In an exemplary aspect, a nonionic surfactant available on the market under the trade name of "Pluronic" is included as an additional surfactant in the compositions. These compounds are formed by condensing ethylene oxide with a hydrophobic base formed by the condensation of propylene oxide with propylene glycol. The hydrophobic portion of the molecule has a molecular weight of from about 1,500 to 1,800. The addition of polyoxyethylene radicals to this hydrophobic portion tends to increase the water solubility of the molecule as a whole and the liquid character of the products is retained up to the point where the polyoxyethylene content is about 50 percent of the total weight of the condensation product.

The semi-polar type of nonionic surface active agents is another class of nonionic surfactant useful in compositions of the present invention. Semi-polar nonionic surfactants include the amine oxides, phosphine oxides, sulfoxides and their alkoxylated derivatives.

Amine oxides are tertiary amine oxides corresponding to the general formula:

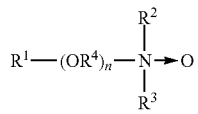

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" Cosmetics & Toiletries, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

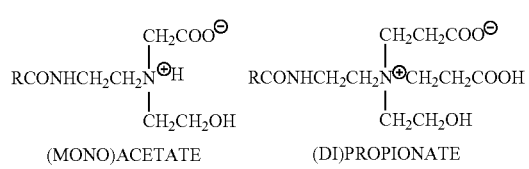

(MONO)ACETATE     (DI)PROPIONATE

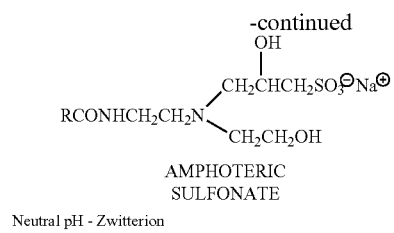

AMPHOTERIC
SULFONATE

Neutral pH - Zwitterion wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+$($CH_2$—$CH_2$—$CO_2Na$)$_2$—$CH_2$—$CH_2$—OH or $C_{12}$-alkyl-C(O)—N(H)—$CH_2$—$CH_2$—$N^+$($CH_2$—$CO_2Na$)$_2$—$CH_2$—$CH_2$—OH. Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate.

Betaine and sultaine surfactants are exemplary zwitterionic surfactants for use herein. A general formula for these compounds is:

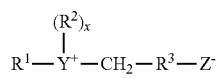

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylaonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

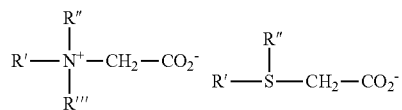

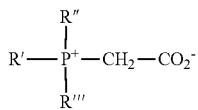

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethyl-amidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N+R^2SO^{3-})$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references is herein incorporated in their entirety.

In an embodiment, the compositions of the present invention include a betaine. For example, the compositions can include cocoamido propyl betaine.

Defoaming Agents

Defoaming agents can also be included in the compositions. Generally, defoamers which can be used in accordance with the invention preferably include alcohol alkoxylates and EO/PO block copolymers. Defoamers can also include polyalkylene glycol condensates and propyl glycols, including polypropyl glycol. In some embodiments, the compositions can include antifoaming agents or defoamers which are of food grade quality given the application of the methods. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. These defoamers can be present at a concentration range from about 0.01 wt-% to 20 wt-%, 0.01 wt-% to 20 wt-%, from about 0.01 wt-% to 5 wt-%, or from about 0.01 wt-% to about 1 wt-%.

Methods of Use

The antimicrobial compositions and virucidal compositions are particularly well suited for treating surfaces in need of antimicrobial efficacy, including for example virucidal efficacy. In further aspects, the antimicrobial compositions and virucidal compositions are still further well suited for treating surfaces in need of virucidal efficacy against small, non-eveloped viruses, large, non-enveloped viruses and/or any enveloped viruses. In a particular, aspect, the antimicrobial compositions and virucidal compositions are particularly well suited for treating surfaces in need of inactivating small, non-eveloped viruses including Norovirus. Accordingly, methods of using an antimicrobial are encompassed according to the present disclosure. Methods of inactivating a virus are also encompassed according to the present disclosure. Methods of inactivating a small, non-enveloped virus are also encompassed according to the present disclosure. Still further, methods of inactivating a Norovirus are encompassed according to the present disclosure.

The methods of use for antimicrobial, including antiviral, disinfection along with inactivating viruses, include a contacting step, wherein the antimicrobial compositions and virucidal compositions disclosed herein are applied to a surface in need of treatment. In an aspect, contacting the composition is to a surface contaminated with a virus, including enveloped and non-enveloped viruses, such as a calciform virus including Norovirus. In a preferred aspect, the methods of use provide complete kill of Norovirus. Beneficially, in an aspect, complete kill of Norovirus on a surface is achieved with a contact time of less than 10 minutes, less than 5 minutes, less than 2 minutes, less than 1 minute, or less than 30 seconds.

In a further aspect, contacting the composition is to a surface contaminated with a biofilm. As referred to herein, a biofilm is often formed on surfaces in contact with water, providing a hydrated matrix of polysaccharides to provide structural protection from biocides and antimicrobial agents, making biofilm more difficult to kill than other pathogens. The contacting step can include providing the antimicrobial compositions and/or virucidal compositions to a hard surface in contact with biofilm, such as for example, walls, floors, sinks, countertops, drain lines, pipes and other plumbing surfaces, tubes and valves and like. Exemplary industries in which the methods and compositions may be used include, but are not limited to, institutional industries, including hotels, housekeeping and foodservice; food processing; water care industries; janitorial industries; and health care. According to embodiments of the methods, the contacting step reduces and/or eliminating biofilm growth produced by a wide variety of bacteria and other microorganisms. For example, according to an embodiment, the methods for treating a biofilm are effective for biofilm comprising a variety of pathogens, such as both gram positive and negative bacteria, including for example *Pseudomonas aeruginosa*, *Escherichia coli*, *Staphylococcus epidermidis*, *Staphylococcus aureus* and *Listeria monocytogenes*.

In a further aspect, contacting the antimicrobial composition and/or and virucidal composition can be to a food contact and/or non-food contact hard surface. Such surfaces can further include instruments, such as medical instruments. Surfaces can also include those cleaned in third-sink sanitizing, including various wares. In still further aspects, contacting the composition can be to a CIP (clean in place) application.

In still further aspects, contacting the composition can be to a ware wash machine, such as a ware wash application.

In still further aspects, contacting the composition can be to a third sink sanitizing application. In a still further aspect, the contacting is beneficially compatible with first sink detergents, such that a third sink sanitizing step could be used as a water recycle to combine with a first sink detergent. This is a benefit over conventional compositions containing quaternary ammonium compounds which are not compatible with first sink detergents.

In still further aspects, contacting the composition can be to a tissue surface, including tissue treatment applications. Exemplary tissue surfaces include mammalian skin, such as animal or human skin, including for example human hands.

The various surfaces to which the compositions can be applied can include any conventional application means. Application can include, for example, by wiping, spraying, dipping, immersing, or the like. The contacting can also include providing a solid to be first dissolved in water to form a solution for the contacting. The contacting step allows the composition to contact the soiled surface for a predetermined amount of time. The amount of time can be sufficient to allow, including from a few seconds to an hour, from about 30 seconds to about 15 minutes, or any range therebetween. The methods may comprise a single step of applying the composition onto the surface without direct physical removal, such as a rinse step. Beneficially, the compositions provide a no-rinse application.

In some aspects, the methods can further include a pre-cleaning step, such as where a cleaning compositions is applied, wiped and/or rinsed, and thereafter followed by the applying of the compositions. The compositions and methods of use thereof can include treating cleaned or soiled surfaces. In some embodiments the amount of contact time between the composition and the surface is sufficient to reduce the population of microorganisms (including Norovirus) on or in a biofilm-soiled surface to provide greater than a 90% reduction (1-log order reduction), greater than 99% reduction (2-log order reduction) in such population, greater than 99.9% reduction (3-log order reduction) in such population, greater than 99.99% reduction (4-log order reduction) in such populations, or greater than a 99.999% reduction (5-log order reduction) in the population of microorganisms and pathogens.

Beneficially, the methods do not require a rinse step. In an aspect, the compositions are food contact approved and do not require a rinse step. As a further benefit, the methods do not cause corrosion and/or interfere with surfaces (e.g. hazy, dull or other negative aesthetic effects on the surface).

The methods can optionally include the use of various sensors and/or indicators. In an aspect, the level of active ingredients in use solution can be monitored by various ways. In one approach, the critical pH of the solution at which the product will start to lose its biocidal efficacy significantly is visually indicated by a color change, and the color change is achieved by choosing a dye that show dramatic color change at this pH. The dye could be simply incorporated into the product, and preferably the dye is incorporated into a polymeric substrate to form a color change strip, and the strip will put in the container, for example the $3^{rd}$ sink to show the color change when the solution pass the critical pH value. Additionally, the level of anionic surfactants in use solution could also be monitored by a similar manner, where a color change will indicate the critical concentration of anionic surfactant needed for biocidal efficacy.

In an additional embodiment, as an alternative to visual indicators, properties of the use solution including pH, anionic activity, fluorescence, and/or conductivity can be monitored by sensors that provide a visual or audible signal when the solution is no longer within a specified range. In some embodiments, a marker molecule can be added to the composition, where the change of the active ingredients in the use solution will trigger the physical and/or chemical property changes of the marker molecule, and the change is quantified through a signal processing.

As a further benefit over the use of quaternary ammonium compounds as are found in various conventional antimicrobial compositions, the antimicrobial and antiviral compositions disclosed herein do not adsorb on the treated surfaces, such as soft surfaces, including for example, microfiber cloths, mops, coated surfaces, etc.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Norovirus Test Protocol. (Examples 1-4)

Samples were prepared to provide the active level of chemistry listed in the tables in 400 ppm hard synthetic water. Synthetic water was AOAC hard water of 400 ppm calcium carbonate. The pH of these solutions was measured and recorded.

Feline calicivirus (FCV) strain VR782 is the surrogate for norovirus efficacy evaluations and tested following ASTM E1053-11 5% Fetal Bovine Serum was selected as the organic soil. Chemistry was tested in duplicate over three different tests for a total of six replicates with complete inactivation (no surviving organisms) required of all replicates to be considered a passing result. In Examples 1-4, the virus titer was 6.5-7 log. If a failure was observed before six replicates were tested the test was ended and reported as a failure. Examples 1-4 show a high challenge test that identifies chemistries that are robustly able to reduce viral populations in support of public health and food safety interests.

The following abbreviations are used in the Examples for components of evaluated formulations:
LAS: anionic surfactant, linear alkyl benzene sulfonic acid
MSA: acid, methane sulfonic acid
DOS: anionic surfactant, sodium dioctyl sulfosuccinate
SAS: acid, sodium bisulfate
Pluronic F68: nonionic surfactant, difunctional block copolymer surfactant ending in primary hydroxyl groups
Pluronic 17R4: nonionic surfactant, difunctional block copolymer surfactant, Poly(propylene glycol)-block-poly(ethylene glycol)-block-poly(propylene glycol), PPG-PEG-PPG
SXS: hydrotope, sodium xylenesulfonate Example 1

Five Minute Efficacy Evaluations. Samples were prepared in 400 ppm synthetic water (SW) with the active level of chemistry outlined in Table 3. Efficacy of compositions was evaluated with a 5 minute contact time according to the norovirus test protocol outlined above. Composition 1-2 utilizing a blend of weak acid (lactic) and strong acid (MSA) was able to provide complete inactivation of the test organism while Composition 1-1 utilizing only a strong acid (sulfuric acid) did not provide complete inactivation of the test organism, despite the compositions having very similar pH values (2.4 and 2.5, respectively).

TABLE 3

| Sample ID | LAS (ppm) | Sulfuric Acid (ppm) | Lactic Acid (ppm) | MSA (ppm) | Pluronic F68 (ppm) | pH in 400 ppm SW supply | 5 Minute Efficacy Outcome |
|---|---|---|---|---|---|---|---|
| 1-1 | 400 | 172 | 0 | 0 | 200 | 2.5 | Fail at 5 minutes |
| 1-2 | 430 | 0 | 1500 | 395 | 200 | 2.4 | 3/3 Pass at 5 minutes |

The results indicate that acid selection impacts outcome of the efficacy against the test organism. Based on the results it is hypothesized that additional strong acid concentration in Composition 1-1 and/or the addition of a weak acid to Composition 1-1 may result in a passing efficacy outcome. Therefore, additional testing was completed.

Example 2

30 Second Efficacy Evaluations for FCV Norovirus Contact. Samples were prepared in 400 ppm SW with the active level of chemistry outlined in Table 4. Efficacy of the evaluated compositions was evaluated with a 30 second contact time following the norovirus test protocol outlined above.

TABLE 4

| Sample ID | LAS (ppm) | Lactic Acid (ppm) | MSA (ppm) | 30 second efficacy outcome | pH in 400 ppm SW supply |
|---|---|---|---|---|---|
| 1-2 | 430 | 1500 | 395 | fail | 2.4 |
| 2-2 | 430 | 1500 | 735 | fail | 2.1 |
| 2-4 | 650 | 1500 | 490 | fail | 2.2 |
| 2-5 | 650 | 1500 | 660 | pass | 2.1 |

As shown in the table, Composition 1-2 which provided complete inactivation at a 5 minute contact time in Example 1 did not provide complete inactivation of the test organism with a 30 second contact time. In addition, even at a pH of 2.1, Composition 2-2 having 430 ppm LAS did not provide complete inactivation of the test organism with a 30 second contact time. When LAS concentration was increased to 650 ppm, complete inactivation of the test organism was achieved at a pH of 2.1 for Composition 2-5. Although complete inactivation was observed, the low pH range may not be preferred for treatment of certain surfaces, as the compositions prepared in a lower alkaline water supply would result in a use solution pH below pH 2.0. Based on these results additional evaluations were required to determine the contribution of lactic acid on efficacy performance as well as the addition of another anionic surfactant to identify compositions having a higher pH range able to support a 30 second efficacy claim.

Example 3

30 Second Efficacy Evaluations for FCV Norovirus Contact—Lactic Acid Efficacy Contribution. Samples were prepared in 400 ppm SW with the active level of chemistry outlined in Table 5. Efficacy of compositions was evaluated with 30 second, 60 second, 1, 2, and 5 minute contact times following the norovirus test protocol outlined above.

TABLE 5

| Sample ID | LAS (ppm) | Lactic Acid (ppm) | MSA (ppm) | 30 Second Efficacy Outcome | 60 Second Efficacy Outcome | 2 Minute Efficacy Outcome | 5 Minute Efficacy Outcome | pH in 400 ppm SW supply |
|---|---|---|---|---|---|---|---|---|
| 1-2 | 430 | 1500 | 395 | Fail | Fail | Fail | Pass | 2.4 |
| 2-4 | 650 | 1500 | 320 | Fail | Fail | n/a | n/a | 2.3 |
| 3-1 | 650 | 2250 | 250 | Fail | Fail | n/a | n/a | 2.4 |
| 3-2 | 650 | 3000 | 230 | Pass | n/a | n/a | n/a | 2.3 |
| 3-3 | 540 | 2250 | 290 | Failure | Fail | n/a | n/a | 2.4 |
| 3-4 | 540 | 3000 | 180 | Pass | n/a | n/a | n/a | 2.5 |
| 3-5 | 540 | 3000 | 0 | Fail | n/a | n/a | n/a | 2.6 |
| 3-6 | 650 | 3000 | 0 | Fail | n/a | n/a | 2/2 weeks pass | 2.6 |
| 3-7 | 540 | 0 | 610 | Fail | n/a | n/a | n/a | 2.3 |
| 3-8 | 540 | 4600 | 0 | Fail | n/a | n/a | n/a | 2.6 |

Complete inactivation of the test organism was achieved with a 30 second time point at a LAS concentration as low as 540 ppm when lactic acid was increased to 3000 ppm for Compositions 3-2 and 3-4. Complete inactivation of the test organism was not achieved with lower concentrations of lactic acid studied at similar or lower use solution pH.

Example 4

Evaluation of Additional Anionic surfactant. Samples were prepared in 400 ppm SW with the active level of chemistry outlined in Table 6. Efficacy of compositions was evaluated with a 30 second and 60 second contact time following the norovirus test protocol outlined above.

TABLE 6

| Sample ID | LAS (ppm) | DOS (ppm) | Lactic Acid (ppm) | MSA (ppm) | Pluronic F68 (ppm) | pH in 400 ppm SW supply | Efficacy outcome 30 seconds | Efficacy outcome 60 seconds |
|---|---|---|---|---|---|---|---|---|
| 1-2 | 430 | 0 | 1500 | 395 | 200 | 2.4 | Failed | Failed |
| 4-1 | 400 | 400 | 1500 | 470 | 200 | 2.4 | Failed | Pass |

The results show that incorporating a second anionic into Composition 4-1 supported complete inactivation of the test organism at a 60 second contact time.

Example 5

Cleaning Performance Evaluations of Residues from the Cleaning Composition. Samples were prepared in 5 grain water with the active level of chemistry outlined in Table 7. 0.5 g of test substance was added to a piece of cheesecloth. The hard surface was wiped and allowed to air dry (about 10 minutes). A visual assessment of the surface was ranked on a scale of 1-5 with 1 having the best appearance.

TABLE 7

| Sample ID | Test products | Active Chemistry | LAS (ppm) | Lactic Acid (ppm) | MSA (ppm) | Pluronic F68 (ppm) |
|---|---|---|---|---|---|---|
| 5-1 | PURE | Silver citrate | n/a | n/a | n/a | n/a |
| 5-2 | Purell Professional | Ethanol | n/a | n/a | n/a | n/a |
| 5-3 | LAS 590 ppm MSA | LAS | 540 | 0 | 590 | 200 |
| 5-4 | LAS 4600 ppm LA | LAS | 540 | 4600 | 0 | 200 |
| 5-5 | LAS 6A | LAS | 540 | 3000 | 180 | 200 |

As shown in FIG. 1, the LAS and acid cleaning compositions according to embodiments of the disclosure show a significant visual improvement over commercially-available products Pure and Purell on all evaluated surfaces. The chemistries employing a strong acid (LAS 590 ppm MSA), weak acid (LAS 4600 ppm LA), and strong/weak acid (LAS 6A) all outperform the commercially-available products with regard to visual assessments of surface cleaning appearance. This evaluation is important to ensure cleaning compositions do not result in, hazy or tacky surfaces. Although the visual assessment of the weak acid (LAS 4600 ppm LA) and strong/weak acid (LAS 6A) compositions ranked equivalently, there were preferred results obtained for the strong/weak acid (LAS 6A) due to formulations benefits obtained by the combination of acids.

Example 6

Corrosion Evaluations. Samples were prepared in 5 grain water with the active levels of chemistry outlined in Table 8. pH of solutions were measured and recorded. Test chemistry was prepared in 5 grain water unless otherwise noted.

TABLE 8

| Sample ID | LAS (ppm) | Lactic Acid (ppm) | MSA (ppm) | Pluronic F68 (ppm) | pH in 5 grain water | pH in 400 ppm SW |
|---|---|---|---|---|---|---|
| 3-4 | 540 | 3000 | 180 | 200 | 2.5 | 2.5 |
| 3-7 | 540 | 0 | 610 | 200 | 2.2 | 2.3 |
| 3-8 | 540 | 4600 | 0 | 200 | 2.6 | 2.6 |
| 6-1 | PURELL (RTU, pH 12.9) | | | | | |
| 6-2 | PURE (RTU, pH 1.8) | | | | | |
| 6-3 | 5 grain water | | | | | |

Weight, height, width, and depth of 1"×2" Aluminum 6061 Coupons were measured and recorded. Coupons were added to sample jar containing 50 mL of test chemistry and exposed for 3 days in a 50C oven. The exposure time period is representative of approximately 5 years of life of a ware if exposed to chemistry 1 min, 2×/day, 365 days/year. After the specified exposure period, aluminum coupons were removed from solution, rinsed with DI water, and allowed to dry. Samples were visually assessed and remeasured. The visual assessment and % change data is provided in Table 9 representing 3 day exposure results.

TABLE 9

| Sample # | LAS (ppm) | Lactic Acid (ppm) | MSA (ppm) | Visual Change | % Mass Change | % Depth Change | % Height change | % Width Change |
|---|---|---|---|---|---|---|---|---|
| 3-4 | 540 | 3000 | 180 | Shiny | 0.00% | −1.25% | 0.00% | 0.08% |
| 3-7 | 540 | 0 | 610 | Slightly Dulled | 0.00% | −0.63% | 0.02% | 0.00% |
| 3-8 | 540 | 4600 | 0 | Shiny | 0.00% | −0.63% | 0.00% | −0.08% |
| 6-1 | | PURE | | Brown Discoloration that washed away with DI rinse, Shiny | 0.00% | −0.63% | 0.00% | 0.20% |
| 6-2 | | PURELL | | Significantly darkened, altered, dull surface | 2.41% | 4.40% | 0.04% | 0.28% |
| 6-3 | | 5 Grain Water | | Brown Discoloration | −0.18% | −0.63% | 0.00% | 0.24% |

As shown in Table 9, the visual changes documented show the evaluated compositions employing a strong acid and/or weak acid all outperform the commercially-available Purell product with regard to lack of corrosion on the treated surfaces.

Example 7

Corrosion Evaluations with Varying Acid Pairs. Samples were prepared in DI water by making a 1 oz./gal dilution of the concentrate formulations outlined in Tables 10A-10C. pH of solutions were measured and recorded. Aluminum 6061 Coupons were added to a sample jar containing test chemistry and exposed for approximately 12 hours, 24 hours, 3 days, 1 week, 2 weeks and 4 weeks' time points in a 50° C. oven. After the specified exposure periods, aluminum coupons were removed from solution, rinsed with DI water, and allowed to dry.

TABLE 10A

| | Formula Name | |
|---|---|---|
| | A4-MSA | A4-SAS |
| LAS (96%) | 5.38 | 5.38 |
| Pluronic F68 | 2.58 | 2.58 |
| Citric Acid (anhydrous) | 13.93 | 13.86 |
| MSA (70%) | 8.99 | 0 |
| Sodium Bisulfate (anhydrous) | 0 | 6.02 |
| Phosphoric Acid (75%) | 0 | 0 |
| SXS (40%) | 18.17 | 4.18 |
| DI H20 | 50.95 | 67.98 |

TABLE 10B

| Formula Name | B1-MSA | B2-MSA | B3-MSA | B4-MSA | B1-SAS | B2-SAS | B3-SAS | B4-SAS |
|---|---|---|---|---|---|---|---|---|
| LAS | 5.38 | 5.38 | 5.38 | 5.38 | 5.38 | 5.38 | 5.38 | 5.38 |
| Pluronic F68 | 2.58 | 2.58 | 2.58 | 2.58 | 2.58 | 2.58 | 2.58 | 2.58 |
| Lactic Acid (88%) | 68.90 | 55.98 | 43.06 | 17.23 | 68.90 | 55.98 | 43.06 | 17.23 |
| MSA (70%) | 0.00 | 2.60 | 5.21 | 10.41 | 0.00 | 0.00 | 0.00 | 0.00 |
| Sodium Bisulfate | 0.00 | 0.00 | 0.00 | 0.00 | 0.00 | 2.37 | 4.73 | 9.46 |
| Phosphoric Acid (75%) | 0.00 | 0.00 | 0.00 | 0.00 | 0.00 | 0.00 | 0.00 | 0.00 |
| DI H20 | 23.14 | 33.46 | 43.77 | 64.41 | 23.14 | 33.69 | 44.25 | 65.36 |

TABLE 10C

| | Formula Name | | | |
|---|---|---|---|---|
| | B1-H3PO4 | B2-H3PO4 | B3-H3PO4 | B4-H3PO4 |
| LAS | 5.38 | 5.38 | 5.38 | 5.38 |
| Pluronic F68 | 2.58 | 2.58 | 2.58 | 2.58 |
| Lactic Acid (88%) | 68.90 | 55.98 | 43.06 | 17.23 |
| MSA (70%) | 0.00 | 0.00 | 0.00 | 0.00 |
| Sodium Bisulfate | 0.00 | 0.00 | 0.00 | 0.00 |
| Phosphoric Acid (75%) | 0.00 | 1.33 | 2.66 | 5.31 |
| DI H20 | 23.14 | 34.73 | 46.32 | 69.51 |

Samples were visually assessed and gloss of coupon was measured. Gloss data was used as a metric to capture dullness of coupon. The lower the gloss value the more change observed of the coupon. The results are shown in Table 11 reporting pH and 20° Gloss Data. The results show preferences for combinations of strong and weak acids according to embodiments of the compositions. For example, the difference in results between B4-MSA and B4-SAS (sodium bisulfate) show the MSA strong acid-containing composition provides approximately a 4 times lower dulling to the treated surface (where the higher the gloss number is indicting of a shiny surface as opposed to a dulled surface). Similarly, the difference in results between B4-MSA and A4-MSA show the lactic weak acid containing composition provides approximately a 4 times lower dulling to the treated surface (where the higher the gloss number is indicting of a shiny surface as opposed to a dulled surface).

TABLE 11

| Formula Name | pH as supplied | Gloss 12 hours | Gloss 1 day | Gloss 3 days | Gloss 7 days | Gloss 14 days | Gloss 21 days | Gloss 28 days | Stdev 12 hr | Stdev 1 day | Stdev 3 day | Stdev 7 days | Stdev 14 days | Stdev 21 days | Stdev 28 days |
|---|---|---|---|---|---|---|---|---|---|---|---|---|---|---|---|
| B1-MSA | 2.451 | 218 | 188 | 141 | 82.3 | 66.1 | 37.8 | 13.2 | 0.5 | 2.8 | 0.2 | 2.2 | 0.3 | 2 | 0.8 |
| B3-MSA | 2.33 | 186 | 223 | 112 | 35.5 | 26.5 | 16.7 | 13.1 | 3.6 | 1.4 | 10.4 | 3.5 | 4.5 | 2 | 2.6 |
| B3 - SAS | 2.336 | 53.2 | 61 | 12.5 | 5.8 | 1.2 | 0.9 | 1 | 5.6 | 1.7 | 1.3 | 0.3 | 0 | 0 | 0 |
| B4 - MSA | 2.206 | 171 | 182 | 78.6 | 30.1 | 25 | 10.5 | 4.5 | 3.8 | 3 | 1.8 | 2.8 | 0.8 | 0.6 | 0.3 |
| B4 - SAS | 2.257 | 17.5 | 14 | 7 | 0.8 | 0.8 | 0.8 | 0.8 | 1.6 | 1 | 0.2 | 0 | 0 | 0 | 0 |
| B4 - H3PO4 | 2.384 | 58.1 | 64.5 | 18 | 1.1 | 0.9 | 0.7 | 0.9 | 3.1 | 6.7 | 1.7 | 0 | 0 | 0 | 0 |
| A4 - MSA | 2.175 | 113 | 78.9 | 10.3 | 4.9 | 1.6 | 0.9 | 0.9 | 4.1 | 5.9 | 0.1 | 1.1 | 0.2 | 0 | 0 |
| A4 - SAS | 2.288 | 19.9 | 10.7 | 5.3 | 0.7 | 2.1 | 0.8 | 0.8 | 3.2 | 0.7 | 0.6 | 0 | 0.6 | 0 | 0 |

Example 8

Additional testing was conducted to demonstrate superiority of the antimicrobial compositions compared to commercially-available compositions. The same methods and protocol were used as described in Examples 1-3 with the modification that the titer in these studies ranged from 5-7. Ambient temperature between 20-26° C. was the temperature condition.

In a first study, the Feline Calicivirus (FCV) norovirus surrogate (strain VR782) was evaluated according to Table 13. Formula 1 as shown in Table 12 according to the disclosure combines LAS with acids for antimicrobial efficacy. The Formulation 1 was diluted at 0.20% by wt. A commercial quat formulation containing Bardac 205M multi-quats (3% n-alkyl (50% C14, 40% C12, 10% C16) dimethyl benzyl ammonium chloride, 2.25% octyl decyl dimethyl ammonium chloride, 1-5% ethanol, 1.35% didecyl dimethyl ammonium chloride, 0.9% dioctyl dimethyl ammonium chloride) and chlorine (Sodium Dichloroiso Cyanurate, Dihydrate) were used as controls for efficacy comparisons. The commercial quat formulation has an actives of 15 wt-% and was diluted at 0.53% by wt. The 50 ppm chlorine was diluted to 0.1 g/L.

TABLE 12

| Formula 1 | Wt-% |
|---|---|
| Water | 32.8 |
| LAS (96%) | 13.3 |
| Lactic Acid (88%) | 38.8 |
| MSA (70%) | 10.0 |
| Pluronic 17R4 | 5.0 |
| Additional Functional Ingredient | Remainder |

TABLE 13

| Chemistry | Contact Time | Soil Condition | R1 | R2 | R3 | R4 |
|---|---|---|---|---|---|---|
| Formula 1 (250 ppm) | 30 seconds | no soil | complete inactivation | complete inactivation | complete inactivation | complete inactivation |
| Commercial quat control (400 ppm) | 30 seconds | no soil | 1.25 | 1.00 | — | — |
| Chlorine (50 ppm) | 30 seconds | no soil | complete inactivation | complete inactivation | — | — |

As shown in Table 13, both chlorine and the Formula 1 were able to achieve complete inactivation with a 30 second contact time while the multi-quaternary control formulation was only able to achieve an average of 1.125 log reduction. In a second study, the Murine Norovirus (MNV) surrogate strain was evaluated according to Table 14 using the Formulation 1 of Table 12 diluted to 0.42% by wt. The commercial quat formulation has an actives of 15 wt-% and was diluted at 0.53% by wt. The 50 ppm chlorine (sodium hypochlorite 10%) was diluted to 0.05% by wt. The 100 ppm chlorine (Sodium Dichloroiso Cyanurate, Dihydrate) was diluted to 0.18 g/L. The 200 ppm chlorine (sodium hypochlorite 10%) was diluted to 0.20% by wt. The concentrations selected for evaluation of the chlorine were based on permitted concentrations for no-rinse applications, including 400 ppm active quat, 100 ppm when chlorine is sourced from sodium dichlororisocyanurate dihydrate and 200 ppm when sourced from sodium hypochlorite. In addition the evaluated concentrations are threshold levels of chemistry that have currently accepted odor, residue and corrosion profiles. Therefore, the claimed composition having complete inactivation (or at least a 5 log reduction) of viruses in addition to the no-rinse application feature with desirable odor, residue and corrosion profiles is beneficial. profile Without being limited to a particular benefit of the compositions and methods of use thereof, a no-rinse application is not required. A rinse step can further be employed.

TABLE 14

| Chemistry | Contact Time | Soil Condition | R1 |
| --- | --- | --- | --- |
| Formula 1 (541 ppm) | 1 minute | no soil | 3.25 |
| Formula 1 (541 ppm) | 5 minutes | no soil | complete inactivation (7 log titer) |
| Commercial quat control (400 ppm) | 5 minutes | no soil | 2.5 |
| Chlorine (50 ppm) | 5 minutes | no soil | 0 |
| Chlorine (100 ppm) | 5 minutes | no soil | <1 |
| Chlorine (200 ppm) | 5 minutes | no soil | 1.25 |

As shown in Table 14, the Formula 1 combining an acid and anionic surfactant provides superior outcomes to the commercially-available multi quat composition and chlorine composition controls. Formula 1 demonstrates complete inactivation with a 5 minute contact time. However, under the same condition, the commercially-available multi quat composition was only able to achieve a 2.5 log reduction. 50 ppm chlorine under the same conditions demonstrated no log reduction and 100 ppm chlorine demonstrated less than 1 log reduction.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A liquid virucidal composition consisting of:
   from about 20 wt-% to about 40 wt-% of at least one weak acid consisting of lactic acid, citric acid, and/or malic acid;
   from about 5 wt-% to about 15 wt-% of at least one strong acid consisting of methane sulfonic acid, phosphoric acid, sulfuric acid, and/or sodium bisulfate;
   from about 5 wt-% to about 20 wt-% of at least one sulfonate, sulfate and/or carboxylate anionic surfactant;
   water; and
   optionally at least one additional functional ingredient including nonionic surfactant, solidifying agents, fragrances, and/or dyes,
   wherein the composition is a liquid concentrate having an acidic pH that is non-flammable;
   wherein a use pH of the composition is from about 1.5 to about 4; and
   wherein the composition is a no-rinse virucidal composition effective against Norovirus.

2. The composition of claim 1, wherein the anionic surfactant is a C8-C22 alkyl sulfonate, and/or alpha sulfonated carboxylic acid or its ester.

3. The composition of claim 2, wherein the C8-C22 alkyl sulfonate is linear alkyl benzene sulfonic acid.

4. The composition of claim 1, further comprising the nonionic surfactant, wherein the nonionic surfactant is an alkoxylated nonionic surfactant having an ethylene oxide/propylene oxide (EO/PO) block copolymer.

5. The composition of claim 1, wherein the composition has a use pH from about 2 to about 4.

6. The composition of claim 1, wherein the composition further comprises the at least one additional functional ingredient from about 1 wt-% to about 38 wt %.

7. The composition of claim 1, wherein the at least one weak acid comprises from about 20 wt-% to about 38 wt-% of the composition and the at least one strong acid comprises from about 5 wt-% to about 10 wt-% of the composition.

8. The composition of claim 1, wherein the liquid is saturated onto a wipe substrate.

9. The composition of claim 1, wherein the liquid is provided as a ready to use concentration comprising from about 5 ppm to about 10,000 ppm of the at least one weak acid and the at least one strong acid, and from about 10 ppm to about 6,000 ppm of the anionic surfactant.

10. A method of using a virucidal composition, comprising:
    contacting the virucidal composition of claim 1 to a surface in need of treatment,
    wherein the method does not require a rinse step and the contacting provides antiviral inactivation efficacy against Norovirus of at least a 3-log reduction to complete inactivation.

11. The method of claim 10, wherein the contacting is by wiping, dipping, immersing, or spraying, and wherein the surface is a hard surface, a precleaned hard surface, a surface contaminated with Norovirus and/or biofilm, and/or a human or mammalian tissue.

12. The method of claim 10, wherein the contacting provides complete kill of the Norovirus in less than 1 minute, and wherein the contacting step is at an aqueous use temperature from about 40° F.-160° F.

13. The method of claim 10, wherein the concentrate is diluted at a rate of from about ⅛ oz./gal. to about 2 oz./gal. to form a use solution comprising from about 5 ppm to about 10,000 ppm of at least one acid, and from about 10 ppm to about 6000 ppm of at least one anionic surfactant.

14. The method of claim 10, wherein a sensor and/or indicator is employed to measure and detect at least one of the following: solution pH at which the compositions loses biocidal efficacy, concentration of anionic surfactant in the use solution, fluorescence, and/or conductivity.

15. A liquid virucidal composition consisting of:
    from about 150 ppm to about 700 ppm of at least one strong acid consisting of methane sulfonic acid, phosphoric acid, sulfuric acid, and/or sodium bisulfate and from about 1500 ppm to about 4000 ppm of at least one weak acid consisting of lactic acid, citric acid, and/or malic acid;

from about 400 ppm to about 700 ppm of at least one sulfonate, sulfate and/or carboxylate anionic surfactant;

water; and optionally at least one additional functional ingredient including nonionic surfactant, solidifying agents, fragrances, and/or dyes, wherein the composition is non-flammable;

wherein the pH of the composition is from about 1.5 to about 4; and wherein the composition is a no-rinse viricidal composition effective against Norovirus.

16. The composition of claim 15, wherein the anionic surfactant is a C8-C22 alkyl sulfonate and/or alpha sulfonated carboxylic acid or its ester.

17. The composition of claim 15, wherein the at least one additional functional ingredient is the nonionic surfactant.

18. A method of inactivating a virus, said method comprising:

contacting the virucidal composition of claim 15 to a surface in need of treatment;

wherein the contacting provides antiviral inactivation efficacy against Norovirus of at least a 3 log reduction to complete inactivation within less 1 minute, or preferably less than 30 seconds, and wherein the method does not require a rinse step and does not impart a residue on the treated surface.

19. The method of claim 18, wherein the method further provides efficacy against a small, non-enveloped virus, a large, non-enveloped virus, and/or an enveloped virus.

\* \* \* \* \*